US00PP09780P

United States Patent [19]

Bennett et al.

[11] Patent Number: Plant 9,780

[45] Date of Patent: Jan. 14, 1997

[54] MINIATURE ROSE PLANT NAMED 'SOMETHING FOR JUDY'

[76] Inventors: Cecilia L. D. Bennett, deceased, late of Chula Vista, Calif.; by Susan M. O'Brien, administratrix, 489 Minot Ave., Chula Vista, Calif. 91910

[21] Appl. No.: 582,198

[22] Filed: Jan. 2, 1996

[51] Int. Cl.[6] ..... A01H 5/00

[52] U.S. Cl. ..... Plt./7.1

[58] Field of Search ..... Plt./7.1, 9, 22, Plt./26, 27

[56] References Cited

U.S. PATENT DOCUMENTS

P.P. 4,754 7/1981 Williams ..... Plt./10

*Primary Examiner*—Howard J. Locker

[57] ABSTRACT

The subject of the present disclosure is a new and distinct variety of miniature rose plant, named 'Something For Judy' which is characterized by buds and blooms in shades of pale pink with a blush of deep pink on the outermost petals which age to near red. Blooms of this rose are usually borne one to a stem with hybrid tea form and sprays of 3 to 5 or more. The bush is vigorous, well-branched and produces moderate to heavy blooms.

1 Drawing Sheet

The present invention relates to a new and distinct variety of a hardy, dwarf, bush plant of the miniature class; the variety being primarily characterized as pink blend.

The variety is further characterized by:

Long stemmed blooms of hybrid tea-type form, borne usually one to a stem and in compact sprays of 3 to 5 or more. The blooms are held very erect and well above the foliage.

The plant ranges in height from 18 to 24 inches (45 to 60 cm). The canes are sturdy and erect with moderate branching and medium to heavy foliage covering. The plant is a heavy bloomer that does well either in the greenhouse or outdoors.

The plant has good growth habits, is well-shaped and attractive, bearing numerous leaflets of average size. Asexual reproduction of the new variety by cuttings derived from the plant stem, as performed at Chula Vista, Calif., shows that the foregoing charcteristics and distinctions come true to form and are established and transmitted through succeeding propagations.

The seed parent was Angel Face (U.S. Plant Pat. No. 2,792), and the pollen parent was Big John (U.S. Plant Pat. No. 4,754). It differs from its seed parent in the following ways. It is a miniature rose of the pink blend class, and Angel Face is a floribunda in the mauve class. It differs from its pollen parent in the following ways. It is a pink blend, and Big John is dark red.

The single color photographic view shows, in plain view, a bouquet of 'Something For Judy' in various stages of maturity from bud stage to nearly open bloom stage.

The descriptive matter which follows pertains to roses grown and color values observed in plants and newly opened blooms in the months of March through November of 1995. The plants were grown outdoors in Chula Vista, Calif., and are belived to be accurate standards for this cultivar in similar conditions of soil and climate elsewhere.

Referring now specifically to the new and distinct variety of miniature rose plant named 'Something For Judy', the following is a detailed description thereof in outline; all major color plate identifications being by reference to the British Colour Council Horticultural Chart, except where common terms of color definition are employed.

Type: Hardy, dwarf, bushy, greenhouse or outdoor, exhibition or garden decorative potted plant.

Class: Miniature.

Variety name: Something For Judy.

Flowers borne: Usually one to a stem, but occasionally in sprays of 3 to 5 or more on erect stems with foliage well below the blooms.

Quantity of bloom: Heavy both outdoors or greenhouse grown.

Bud:

*Peduncle.*—Average length (30 to 50 mm); average diameter and sturdy; ranging from near Scheeles Green (860/3 to 860/1 page 176) with occasional tinging of bronze.

*Hairs.*—Extremely small and sparse with a reddish color; located over the surface of the peduncle and calyx tube.

*Calyx.*—Color range same as peduncle.

*Opening.*—Opens well in all weather.

Bloom:

*Size when fully open.13* Slightly larger than average for a miniature variety (45 to 55 mm).

*Petalage.*—Full — 25 to 35 petals, arranged regularly, plus 5 to 10 petaloids.

*Form.*—Urn-shaped to ovoid as the bloom opens. The petals remain somewhat cupped with the apex and/or margins reflexed outward, becoming at maturity more loosely cupped.

Petals: Fairly thick with good substance; both the upper and under surfaces of all petals have a matte finish.

*Shape.*—Outer petals are of a broad obovate form. The intermediate petals are very much like the outer petals only narrower. The inner petals are a broad lanceolate form; and the petaloids are also lanceolate with some occasional irregularities.

Color: Newly opened flowers from plants grown outdoors (March through November of 1995), Chula Vista, Calif.

*Inner petals.*—Upper and under surfaces — Ranging from near Orient Pink (416/3 to 416/2 page 124) to near shell Pink (516/3 to 516/2 page 135).

*Outer petals.*—Upper surfaces— Ranging from near Orient Pink (416/3 to 416/2 page 124) to near Shell Pink (516/3 to 516/2 page 135) at the base with a blush on the outer margins which ranges from near Azalea Pink (618/1 to 618 page 74) to near Scarlet (19/2 to 19/1 page 19) NOTE: Blush spreads across and deepens on all sun-exposed surfaces of blooms, especially in warmer climates. Blush is paler on blooms grown in cooler climates or during overcast or cloudy days.

Under surfaces — Ranging from near Orient Pink (416/3 to 416/2 page 124) to near shell Pink (516/3 to 516/2 page 135) with only occasional blush of near Azalea Pink (618/2 to 618/1 page 74) on the outermost petals.

*General color effect.*—Newly opened flowers — Pale pink with a darker pink to scarlet blush on the outermost petals. Three to five days open —Pink blush on the outermost petals begins to darken and spread to all sun-exposed petal surfaces. After five days— Fully open blooms will appear deep pink to scarlet in sunny/warmer climates; while open blooms in cooler/cloudy climates will remain pale pink with a deeper pink blush only on outermost petals.

*Flower longevity. (March through November* 1995).— Plant in pot 3 to 5 days from bud with sepals reflexed to fully open bloom. Holding at fully opened for 5 to 7 days longer. Cut blooms at living room temperature 10 to 14 days or longer.

Reproductive organs:

*Stamens.*—A generous amount arranged uniformly around the pistil.

*Filaments.*—Varying in length with shorter filaments more proximal to the pistil; pale yellow in color with anthers of golden yellow.

*Pollen.*—Abundant.

*Pistil.*—Short, spreading and abundant; pale yellow.

*Ovaries.*—All encased in calyx.

*Hips.*—Some.

*Seeds.*—3 to 5 days or more in each hip.

Foliage:

*Sepals.*—Permanent; simple and glabrous; spear-shaped; open as the bloom opens, recurving against the peduncle, when the bloom is fully opened. Ocasional foliaceous appendages attractively supplement sepal terminals; these are of varying lengths.

*Leaves.*—5 to 7 leaflets on average; medium size for a miniature rose plant.

*Leaflets.*—Broad ovate-shaped.

*Margins.*—Very serrated with tinting of bronze, especially noticeable on the newer foliage.

*Color.*—Ranging from near Spinach Green (0960/3 to 0960 page 187) to near Scheeles Green (860/1 to 860 page 175) with occasional bronzing of the margins especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Dwarf, bush; above average with a miniature rose plant.

*Rate and character.*—Vigorous and well-branched.

*Canes.*—Medium diameter; sturdy; held erect.

*Main stems.*—Color range same as foliage.

*Thorns.*—Averaging less than 5to 10 per 10 cm on the main stems and branches. Reddish in color; average size; slender and hooked slightly downward.

*Branches.*—Coloration ranges the same as does that of the foliage.

The miniature rose plant and its flowers as herein described may vary in slight detal due to climate, soil and cultural conditions under which the variety may be grown; the present description being of the variety as grown in Chula Vista, Calif.

No information related to insect, disease or frost tolerance is available due to the controlled growing conditions under which our plants are produced and maintain, which includes regular application of fungicides and pesticides on all plants and the immediate elimination of any inferior seedlings which demonstrate a tendency to develop diseases or other unpleasant habits. As to frost tolerance, all of our plants are grown in Chula Vista, Calif. which is located in a moderate temperature zone that would rarely experience frost or freezing temperatures. For the above mentioned reasons, the specifications have not been expanded further.

The following is claimed:

1. A new and distinct variety of miniature rose plant, named 'Something For Judy', hardy, dwarf, vigorous growth, well-branched and attractive in appearance, substantially as illustrated and described; characterized by its hybrid tea form blooms, ranging from near Orient Pink to near Shell Pink with darker pink blush on the outermost petals of near Azalea Pink to near Scarlet, which are abundant on the bush and usually borne one to a stem but occasionally in sprays of 3to 5 or more.

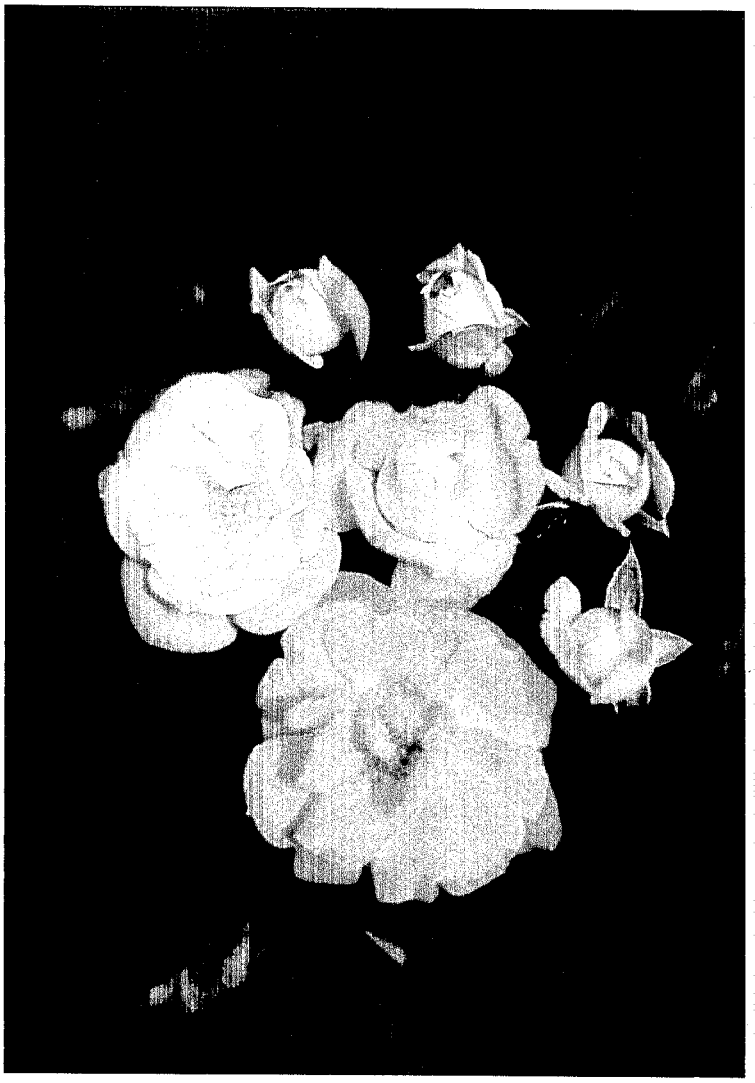

* * * * *